United States Patent [19]

Bryant

[11] Patent Number: 4,797,420

[45] Date of Patent: Jan. 10, 1989

[54] DISINFECTANT FORMULATION AND METHOD OF USE

[75] Inventor: James A. Bryant, Jennings, La.

[73] Assignee: Jabco Manufacturing, Inc., Lake Arthur, La.

[21] Appl. No.: 25,666

[22] Filed: Mar. 13, 1987

Related U.S. Application Data

[63] Continuation of Ser. No. 06/775,030, Sep. 11, 1985, abandoned, which is a continuation-in-part of Ser. No. 06/649,793, Aug. 14, 1984, abandoned.

[51] Int. Cl.$^4$ .................... A01N 33/12; A61K 31/14
[52] U.S. Cl. .................................. 514/643; 514/975
[58] Field of Search ................... 514/643, 975

[56] References Cited

U.S. PATENT DOCUMENTS

| | | | |
|---|---|---|---|
| 2,689,814 | 9/1954 | Nicholls | 424/329 |
| 3,017,278 | 1/1962 | Laff | 514/643 |
| 3,247,119 | 4/1966 | Herrick et al. | 514/643 |
| 4,336,151 | 6/1982 | Like et al. | 514/643 |
| 4,336,152 | 6/1982 | Like et al. | 514/643 |

FOREIGN PATENT DOCUMENTS 653251  3/1979  U.S.S.R. .......................... 424/329

OTHER PUBLICATIONS

Chem. Abst. 67: 51205m (1967)—Sidwell et al.
Chem. Abst. 71: 1039x (1969)—Bydzovsky et al.
Chem. Abst. 85: 137960n (1976)—Tanabe et al.

*Primary Examiner*—Douglas W. Robinson
*Attorney, Agent, or Firm*—Eric P. Schellin

[57] ABSTRACT

A formulation effective against microorganisms including herpes simplex types 1 and 2 viruses, comprising an alkyl (58% $C_{14}$, 28% $C_{16}$, 14% $C_{12}$) dimethyl benzyl ammonium chloride.

10 Claims, No Drawings

DISINFECTANT FORMULATION AND METHOD OF USE

This application is a continuation of application Ser. No. 06/775,030, filed Sept. 11, 1985, now abandoned, which is a continuation-in-part of Ser. No. 06/649,793, filed Aug. 14, 1984, now abandoned.

The present invention relates to a disinfectant cleaner formulation for hard surfaces. The formulation possesses broad spectrum germicidal and virucidal efficacy, and is particularly effective against herpes simplex viruses.

Herpes viruses are ubiquitous in nature; natural hosts include the frog, chicken, mouse, guinea pig, cat, dog, swine, cow, horse, monkey, and man. Man is the natural host for Herpes simplex type 1 and 2, varicella/zoster, cytomegalovirus and Epstein-Barr virus (EBV), and can be a temporary host for herpes B virus of monkeys with serious consequences. Clinical illness caused by herpes viruses presents a significant health problem for which no effective preventive measures have been available. Herpes simplex type 1 and 2 are antigenically related, but generally cause infection at different sites. Herpes simplex type 1 (HSV1) is transmitted by the oral-respiratory route and is most frequently associated with oral lesions. Herpes simplex type 2 (HSV2) is transmitted venereally and is usually responsible for herpes genitalis and neonatal herpes. The role of these viruses in chronic disease has not been defined. However, HSV2 has been implicated in genital cancer on the basis of seroepidemiologic findings, demonstration of herpesvirus antigens or viral nucleic acid in neoplastic tissue, and in vitro transformation of a variety of cells, including human cells, by irradiated virus.

The two types of herpes simplex can be distinguished by serologic examination of the antibodies produced after exposure to the virus, but cannot be differentiated in a culture. The herpes simplex infections are also named after their localization, e.g., herpes labialis, ocular herpes, herpes genitalis, rectal herpes, herpes progenitalis, herpes preputialis, intrauterine herpes, etc. They are also called herpes febrilis, cold sore, or herpes menstrualis, according to the timing of their appearance with the above-mentioned conditions. Both types of herpes, HSV1 and HSV2, can be sexually transmitted and cause lesions in and on the genitals, on thighs, buttocks, or in the mouth and rectum.

Herpes simplex virus can live for hours outside the human body on a variety of materials and surfaces including toilet seats, plastic containers, specula, and gauze, as reported by Larson and Bryson, Int. Med. News 15: 17 (1982). It is actively infective for up to 2½ months in dried crusts from herpetic lesions kept at room temperature, as reported by Nahmias et al, "Transport Media for Herpes Simplex Virus Types I and II", *Appl. Microbiol.* 22:451–454 (1971). Parvey and Chien, "Neonatal Herpes Virus Infection Introduced by Fetal Monitor Scalp Electrodes", *Pediatrics* 65: 1150–1153 (1980), described another possibility of non-sexual transmission of herpes simplex infection in an infant who developed acute herpes meningoencephalitis and pneumatosis intestinalis as a result of fetal monitoring with scalp electrodes on the buttocks. The first vesicles appeared at the site where the electrodes were placed. Montefiore et al., "Herpes Virus Hominis Type II Infection in Ibadan, Problem of Non-Venereal Transmission," *Br. J. Vener. Dis.* 56: 49–53 (1980), report a possibility of non-veneral transmission of herpes hominis type II that could survive for long enough on cloth samples under humid tropical conditions to cause infections. The herpes simplex Hominis virus type I and II are members of a large herpes virus family of which about 70 varieties are known. Those harmful to humans cause birth defects, chicken pox, shingles, mononucleosis, and are associated with malignant diseases.

Various treatments of herpes simplex have been proposed. Asculai, U.S. Pat. No. 4,147,803, teaches that certain sorbitan derivatives have anti-herpetic activity. DeLong et al., U.S. Pat. No. 3,639,612, described such activity for certain chalcogen containing heterocyclic compounds. Stedman, U.S. Pat. No. 3,555,355, discloses that certain cycloalkylamines have activity against herpes simplex. Fleming et al, U.S. Pat. No. 3,829,578, teaches that certain bis-basic ethers and xanthen-9-ones have anti-viral activity. Soichet, U.S. Pat. No. 4,312,884, describes the antiviral activity of Spectinomycin. Other forms of treatment of herpes virus infections include 5-iodo-2-deoxyridine, 9-beta-D-arabino-fluoro-syladenine, topical applications of adenine arabinoside, application of a vital dye as neutral red of proflavine followed by exposure to light, human leukocyte interferon, Acyclovir, lysine, ascorbic acid, topical ether, topical chloroform, tymol, nonionic surfactants, inactivated herpes virus, zinc, urea, tannic acid, glutaraldehyde, cow pox vaccine, intradermal injections of gamma globulins, and a surgical treatment by epidermal excisions of the herpetic lesions. None of these treatments has been exceptionally successful, and to date it appears that the best defense against herpes infection is prevention by an anti-herpes agent.

Ores, in U.S. Pat. No. 4,427,684, discloses that cycloheximide may be used prophylactically as a solution or spray to prevent non-veneral transmission of a viral infection.

A number of quaternary ammonium compounds have been used in the past in germicidal formulations, although none of the compounds so disclosed have been used against herpes simplex viruses. Examples of germicidal formulations incorporating quaternary ammonium compounds include those disclosed in Like et al. . . . U.S. Pat. Nos. 4,336,151 and 4,336,152, wherein a quaternary ammonium compound is combined with a nonionic surfactant, d-limonene, an eye irritancy reducing compound, water, and optionally, a lower aliphatic alcohol. Another disinfectant composition is disclosed by Laff in U.S. Pat. No. 3,017,278. The Laff composition comprises an aqueous solution containing nonyl phenoxy polyoxyethylene ethanol and a high molecular weight alkyl dimethyl benzyl ammonium chloride Herrick et al., U.S. Pat. No. 3,247,229, disclose a cleansing composition for bactericidal uses including a mixture of quaternary ammonium compounds and water. Russian patent No. 653251 discloses a virucide containing dimethyl cetyl benzyl ammonium chloride.

SUMMARY OF THE INVENTION

It has now been discovered that certain formulations can be used to disinfect surfaces and to kill herpes simplex type I and type II, as well as a variety of other microorganisms. The active ingredient in this formulation is an alkyl dimethyl benzyl ammonium halide, such as a chloride or a bromide, wherein the alkyl groups are 58% $C_{14}$, 28% $C_{16}$, and 14% $C_{12}$. The chloride compound is available commerically as Bio-Quat 50-28 from Bio-Lab, Inc. of Decatur, Ga., bearing EPA Reg. No. 5185-36. This particular type of quaternary ammonium compound has been found to be particularly effective against herpes simplex type I and II viruses when used in a suitable carrier and applied to the surface to be treated.

An effective carrier for the particular quaternary ammonium compound of the present invention includes a nonionic surfactant, a lower ($C_1$-$C_4$) alcohol, and water. Suitable fragrance and colors can be added to the formulations to make it more pleasing to the ultimate user.

The quaternary ammonium compound is generally present in the formulation of the present invention in an amount equal to about 0.2 to 10% by weight, with about 3 to 6% by weight preferred.

The nonionic surfactants used in the formulation of the present invention include, but are not limited to, that class of compounds formed by condensation of an alkyl phenol, an alkyl amine, and aliphatic alcohol, or a fatty acid, with sufficient ethylene oxide to produce a compound having a polyoxyethylene chain within the molecule, i.e., a chain composed of recurring (—O—CH$_2$—CH$_2$—) groups. Many compounds of this type ar known. Examples of this type of surfactant are those compounds produced by condensing about 5-30, preferably about 8-16, moles of ethylene oxide with one mole of (1) an alkyl phenol having 0-15, preferably (7-10), carbon atoms in the alkyl group; (2) an alkyl amine having about 10-20, preferably 12-16, carbon atoms in the alkyl group; (3) an aliphatic alcohol having about 9-20, preferably 12-16, carbon atoms in its molecule; and (4) a fatty acid having about 10-20, preferably 12-16, carbon atms in its molecule. A preferred nonionic surfactant is nonylphenol 9.5 mole ethylene oxide adduct The nonionic surfactant generally comprises about 0.1 to about 10% by weight of the formulation.

The lower alcohol used in the formulation according to the present invention is an alcohol having from 1 to 4 carbon atoms in the molecule, including methanol, ethanol, isopropanol, and butanol The preferred alcohol is isopropanol. The alcohol is generally present in the composition in amounts ranging from about 20% to about 90%.

Fragrances can be used to make the formulation more aesthetically pleasing to the ultimate user. Suitable fragrances include methyl salicylate, which imparts a mint odor to the formulation, and lemon oil, which imparts a lemon odor to the formulation. The fragrances can be used in amount ranging form about 0.10% to about 1% by weight, the amount used being dependent on the fragrance used and the desired effect.

Water is the additional carrier for the quaternary ammonium active ingredient. The water is added in a quantity sufficient to bring the total percentage of ingredients up to 100% by weight In order to inactivate or kill herpes simplex viruses or other such microorganisms, the formulation of the present invention is applied directly to the surface to be disinfected. For ease of use, the formulation may be incorporated into a spray-type dispenser whereby it can be sprayed directly onto the surface to be treated. An example of such use would be for a person to spray it on surfaces in public restrooms in order to kill any herpes viruses present in the restroom form others who have used the facilities. Such an action could provide valuable peace of mind to those who are concerned about the possibility of contracting herpes from use of such facilities.

A film of the disinfectant formulation of the present invention dries very quickly, almost instantaneously, and is undetectable. The film, which is water-soluble, is not worn off by friction, and is active for over 24 hours.

DESCRIPTION OF THE PREFERRED EMBODIMENTS

EXAMPLE I

A formulation which has been found to be effective against a variety of viruses, including herpes simplex types 1 and 2, formulated as follows:

Bio-quat 50–28*:2.00% (weight)
Nonylphenol 9.5 mole
ethylene oxide adduct**:0.50
Isopropanol: 80.00
Water: 17.25
Lemon oil: 0.25

* Alkyl ($C_{14}$, 58%, $C_{16}$, 28%, $C_{12}$, 14%) dimethyl benzyl ammonium chloride
** T-det 9.5 Surfactant, Thompson-Hayward Chemical Co.

EXAMPLE II

A formulation specifically disigned to kill herpes simplex viruses on surfaces was made up form the following ingredients Alkyl (58% $C_{14}$, 28% $C_{16}$, 14% $C_{12}$) dimethyl benzyl ammonium chloride: 5.00%
Nonylphenol 9.5 mole
ethylene oxide adduct: 0.50
Isopropanol: 80.00
Water: 14.00
Methyl salicylate: 0.50

The above percentages are all by weight.

The above formulation had a pleasant mint odor and was found to be effective against herpes simplex viruses when applied to surfaces affected by such viruses

EXAMPLE III

A formulation for use against herpes simplex viruses was formulated form the following ingredients:

Alkyl (58% $C_{14}$, 28% $C_{16}$, 14% $C_{12}$) dimethyl benzyl ammonium chloride: 5.00%
Nonylphenol-9.5 mole
ethylene oxide adduct: 0.60
Isopropanol: 80.0
Water: 14.15
Lemon oil: 00.25

The above formulation, which was effective against both type I and type II herpes simplex viruses, had a pleasing lemon fragrance.

EXAMPLE IV

An effective formulation for use against herpes simplex viruses and which can be easily sprayed from a container was made from the following ingredients:

Triton X100*:9.00%
Ethanol: 5.50
Water: 70.00
Methyl Salicylate: 0.50

*Rohm & Haas, octylphenol having about 9 moles of condensed ethylene oxide

EXAMPLE V

Another formulation for use against herpes simplex viruses types I and II was made form the following ingredients:

Alkyl (58% $C_{14}$, 28% $C_{16}$, 14% $C_{12}$) dimethyl benzyl
  ammonium bromide: 2.00%
Neodol 25-9*:10.00
Water: 58.00
Isopropano: 30.00

* Shell chemical Co., ethoxylated mixture of normal and 2-methyl branched primary C12-15 alcohols having about 9 moles of condensed ethylene oxide The formulation of Example I was evaluated in it effectiveness against a variety of viruses and found to be effective at reasonable condensation.

HERPES SIMPLEX TYPE I QUICK KILL TEST

A virucide assay was conducted to determine if the formulation of Example I can inactivate a dried film of virus on a glass surface in a very short period of time. 0.2 ml of virus pool, Herpes simplex type 1 pool #23, ATCC #VR-260 GBL#V-504, was spread onto the surface of glass petri dishes and allowed to dry to a film at 35° C. for 30-45 minutes. Then 2.0 ml of the subject disinfectant was spread over the film and allowed to remain in contact for 30 seconds at 20°-25° C. After 30 seconds, the virus-germicide mixture was removed by pipette and diluted in trypticase soy broth up to $10^{-5}$ to $10^{-7}$. Decimal dilutions were then inoculated into the appropriate host.

It was found that the subject formulation inactivated the herpes simplex type 1 virus within 30 seconds, and therefore exceeds the requirements for a virucide as set forth in the Federal Register, 10, #123, June 25, 1975, p. 26836.

HERPES SIMPLEX TYPE II QUICK KILL TEST

A virucide assay was conducted to determine if the formulation of Example I can inactivate a dried film of virus on a glass surface in a very short period time.

0.2 ml of virus, Herpes simplex type II ATCC#VR-734 Strain G, was spread onto the surface of glass perti dishes and allowed to dry to a film of 35° C. for 30-45 minutes. Then 2.0 ml of the disinfectant of Example II was spread over the film and allowed to remain in contact virus-germicide mixture was removed by pipette and diluted therewith for 30 seconds at 30°-25° C. After 30 seconds, the virus-germicide mixture was removed by pipette and diluted in trypticase soy broth up to $10^{-5}$ to $10^{-7}$. Decimal dilutions were then inoculated into the appropriate host.

It was found that the subject formulation inactivated the herpes simplex type II virus within 30 seconds, and therefore exceeds the requirements for a virucide as set forth in the Federal Register, 10, #123, June 25, 1975, p. 26836.

POLIO VIRUS

The formulation of Example I was tested against polio type I virus, pool #2, ATCC #VR-1000 GBL#V-536, by spreading 0.2 ml of the virus onto the surface of petri dishes and allowed to dry to a film at 35° C. for 30-45 minutes. then, 2.0 ml of the formulation of Example II was therewith for 10 minutes at 20°-25° C. After 10 minutes the virus-germicide mixture was removed by pipette and diluted in trypticase-soy broth up to $10^{-5}$ to $10^{-6}$. Decimal dilutions were then inoculated into appropriate hosts.

A sample of the subject disinfectant at the dilution tested inactivated the polio type I virus and, therefore, meets the requirements for a virucide as set forth in the Federal Register, 10, #124, June 25, 1975, p. 26836.

HERPES SIMPLEX TYPE I

To determine if the formulation of Example I can inactivate a dried film of virus on a glass surface, 0.2 ml of virus pool, herpes simplex type 1, pool #23, was spread onto the surface of glass petri dishes and allowed to dry to a film at 35° C. for 30-45 minutes Then, 2.0 ml of the formulation of Example I was spread over the film and allowed to remain in contact for 10 minutes at 20°-25° C. After 10 minutes, the virus-germicide mixture was removed by pipette and diluted in trypticase soy broth up to $10^{-5}$ to $10^{-7}$ Decimal dilutions were inoculated into appripriate hosts.

A sample of the subject formulation at the dilution tested inactivated the herpes simplex type 1 virus and, therefor, meets the requirements for a virucide as set forth in the Federal Register 10, #123, June 25, 1975, p. 26836.

HERPES SIMPLEX TYPE II

To determine if the formulation of Example I can inactivate a dried film of herpes simplex type II on a glass surface, 0.2 ml of the virus pool #11SMMC was spread onto the surface of glass petri dishes and allowed to dry to a film at 35° C. for 30-45 minutes Then, 2.0 ml of the formulation of Example I was spread over the film and allowed to remain in contact for 10 minutes at 20°-25° C. After 10 minutes, the virus-germicide mixture was removed by pipette and diluted in trypticase soy broth Decimal dilutions were then inoculated into the appropriate host.

The sample of the subject disinfectant at the dilution tested inactivated the cited herpes simplex type II virus and, therefore, meets the requirements for a virucide as set forth in the Federal Register, 10, #123, June 25, 1975, p. 26836.

Herpes Simples Type II—Residual Assay

To determine if a sample of the formulation of Example I possess a sufficient residual effect after 24 hours so as to inactivate herpes simplex type II virus, a delayed contamination experiment was conducted. Two ml. of the formulation of Example I was spread onto a glass surface (petri dish) and allowed to dry. After 24 hours, 0.2 ml. of the virus (pool #12, ATCC #VR-734 stain G) was placed on the dried disinfectant film and allowed to remain in contact for 10 minutes at 20°25° C. After 10 minutes, 1.8 ml. of trypticase soy broth was added to this to obtain o volume of 2.0 ml. ($10^{-1}$ of virus). This mixture was then removed by pipette and diluted in TSB up to $10^{-5}$ to $10^{-6}$. The decimal dilutions were inoculated into the appropriate host.

It was found tht the disinfectant tested displayed a significant residual effect. Herpes simplex virus type II was reduced in titer at least 3 logs when it was placed in contact with a surface that was treated with the virucide 24 hours earlier.

HERPES SIMPLEX TYPE I—RESIDUAL ASSAY

To determine if a sample of the formulation of Example I possesses a sufficient residual effect after 24 hours so as to inactivate herpes simplex type I virus, a delayed contamination experiment was conducted. Two ml. of the formulation of Example I was spread onto a glass surface (petri dish) and allowed to dry. After 24 hours. 0.2 ml of the virus pool (pool #23, GBL 504, ATCC VR-260) was placed onto the dried disinfectant film and allowed to remain in contact for 10 minutes at 20°-25°

C. After 10 minutes, 1.8 ml of trypticase soy broth was added to this to obtain a volume of 2.0 ml($10^{-1}$ of virus). This mixture was then removed by pipette and diluted in TSB up to $10^{-5}$ to $10^{-6}$. The decimal dilution were inoculated into the appropriate host.

The liquid disinfectant tested displayed a residual effect. Herpes simplex virus Type I was reduced in titer at least 3 logs when it was placed in contact with a surface that was treated with virucide 24 hours earlier.

INFLUENZA B VIRUS

The formulation of Example II was tested for its efficacy against Influenza B viruses. The virus used was ATCC #1 VR-102 GBL#V-520. A pool of 0.2 ml of virus was spread onto the surface of glass petri dishes and allowed to dry to a film at 35° C. for 30–45 minutes. Then, 2.0 ml of the formulation of Example I was spread over the film and allowed to remain in contact for 10 minutes at 20°–25° C. After this time, the virus-germicide mixture was removed by pipette and diluted in trypticase soy broth up to $10^{-5}$ to $10^{-7}$. Decimal dilutions were then inoculated into appropriate hosts.

It was found that the subject disinfectant, at the dilution tested, inactivated Influenza B virus and meets the EPA requirements for a virucide as set forth in the Federal Register, 10, #123, June 25, 1975.

Acute toxicity tests were performed as per the methods of (1) Draize et al. in "Appraisal of the Safety of Chemicals in Foods, Drugs, and Cosmetics", Assoc. of Food and Drug Officials of the U.S., (1965) P.O. Box 1494, Topeka, Kans.; (2) Marzulli, F. N. and Ruggles, D. I., *Jour. AOAC* 56 (1973); (3) Federal Hazardous Substances Act, DFR 16, Chapter 11, Parts 1500.3, a500.40, 1500.41, 1500.42.

0.5 ml of the formulation of Example I was applied under gauze dressing to the clipped intact and abraded skin edema at 24 and 72 hours. The formulation of Example I produced a skin irritation score of 1.5 (A score of 5 or more is considered a primary irritatnt), and was thus considered to be slightly irritating.

PSEUDOMONAS, STAPHYLOCOCCUS, AND SALMONELLA

In order to determine the efficacy of the formulation of the present invention against a variety of microorganisms, the formulation of Example II was tested against the following microrganisms:
Pseudomonas aeruginosa ATCC#15422
Staphylococcus aureus ATCC#6538
Salmonella cholerasuis ATCC#10708

Stainless steel penicylindrs were pre-soaked overnight in 1N NaOH, washed in water, and autoclaved in 0.1% asparagine. Anatone nutrient broth was used for preparation of the organisms. Letheen, broth, 4.001 d. 3, 10 ml per tube, was used for subculture recovery of organisms from medicated carrier. Culture was for 48–54 hours, Anatone nutrient broth at 37° C., representing transfers originally derived form 4 consecutive 24 hour serial subcultures form nutrient agar slant stock.

The cylinders were immersed for 15 minutes in 20 ml. of the culture of the particular organisms tested, and were then dried on filter paper in a sterile petri dish at 35° C. for 20–60 minutes.

Each contaminated and dried carrier was placed into a separate tube of the formulation of Example II diluted to 2% active ingredients for 10 minutes at 20°–25° C. Each medicated carrier was then transferred by hook needle at 1 minute staggered intervals to 10 ml of recovery broth.

The formulation of Example II passed an AOAC Use Dilution Test against *S. aureus, Ps. aeruginosa* and *Sal. cholerasuis,* producing 0/60, 0/60, and 1/60 positive, respectively.

INFLUENZA VIRUS

Influenza virus A2 J-305 pool #59 (Asan A2 57/305) was spread onto the surface of a glass petri dish (0.2 ml of virus) and allowed to dry to a film at 35° C. for 30–45 minutes. Two ml of the formulation of Example II was Spread over the film and allowed to remain in contact for 10 minutes at 20°–25° C. After 10 minutes the virus-germicide mixture was removed by pipette and diluted in trypticase soy broth up to $10^{-5}$ to $10^{-7}$. Decimal dilutions then were inoculated into appropriate hosts.

It was found that the formulation of Example II at the dilution tested inactivated the cited virus and, therefore, meets the requirements for a virucide as set forth in the Federal Register 10, #123, June 25, 1975, p. 26836.

ADENO VIRUS

A pool of adeno virus type 2, pool #36 (0.2 ml) was spread onto the surface of petri dishes and allowed to dry to a film at 35° C. for 30–45 minutes. Then, 2 ml. of the formulation of Example II was spread over the film and allowed to remain in contact for 10 minutes at 20°–25° C. After 10 minutes, the virus-germicide mixture was removed by pipette and diluted in trypticase soy broth for up to $10^{-5}$ to $10^{-7}$. Decimal dilutions were then inoculated into appropriate hosts A sample of the subject disinfectant at the dilution tested inactivated the cited virus and, therefore, meets the requirements for a viruciode as set for the in the Federal Register, 10, #123, June 25, 1975, p. 26836.

TRICHOPHYTPN

In order to test the efficacy of the formulation of Example II against fungi, the formulation of Example II was used to contact a 0.5 ml spore suspension of *Trichophyton mentagrophytes* (GBL #334), ATCC #9533, for 5, 10, and 15 minutes. The subculture was incubated for 10 days at 25° C.

The formulation of Example II was found to pass an ADAC fungicidal test against *Trichophyton mentagrophytes.*

VACCINIA

The formulation of Example II was used against Vaccinia V-506, pool #37. A pool of virus (0.2 ml) was spread onto the surface of glass petri dishes and allowed to fry to film at 35° C. for 30–45 minutes. Then, 2.0 ml of the formulation of Example II was spread over the film and allowed to remain in contact therewith for 10 minutes at 20°–25° C., After 10 minutes, the virus-germicide mixture was removed by pipette and diluted in trypticase soy broth up to $10^{-6}$ Decimal dilutions were then inoculated into the appropriate hosts.

The subject disinfectant tested was found to inactivate the cited virus, and therefore meets the requirements for a virucide as set forth in Federal Register, 10, #123, June 25, 1975, p. 26836.

While several embodiments of this invention are shown above, it will be understood that the invention is not to be limited thereto, since many modifications may be made, and it is contemplated, by the appended claims, to cover any such modifications as fall within the true spirit and scope of this invention.

What is claimed is:

1. A quick drying virucide formulation for killing microroganisms selected from the group consisting of herpes simplex type 1 and herpes simplex type 2 comprising a mixture consisting essentially of about 0.2 to about 10 by weight of alkyl (58% $C_{14}$, 28 $C_{16}$, 14% $C_{12}$) dimethyl benzyl ammonium halide, 20 to 90% by weight of a lower $C_1$–$C_4$ aliphatic alcohol, 0.1 to 10% by weight of nonionic surfactant formed by condensing a compound selected from the group consisting of an alkyl phenol, an alkyl amine, an aliphatic alcohol or a fatty acid with ethylene oxide, and a remainder of water.

2. The formulation of claim 1 wherein the lower alcohol is isopropanol.

3. The formulation of claim 2 wherein the nonionic surfactant is a nonylphenol 9.5 mole ethylene oxide.

4. The formulation of claim 2 wherein the halide is a chloride.

5. The formulation of claim 1 wherein the halide is present in amounts ranging from about 0.2 to about 10% by weight, the nonionic surfactant is present in amounts ranging from about 0.1 to about 10% by weight, the lower alcohol is present in amoung ranging from about 20 to about 90% by weight, and the remainder of the formulation is water.

6. The formulation is claim 5 wherein a fragrance is present in amounts ranging from about 0.01 to about 1% by weight.

7. A method for killing microorganisms selected from the group consisting of herpes simplex type 1 and herpes simplex type 2 comprising, applying to hard surfaces an effective amount of a quick drying virucide mixture consisting essentially of about 0.2 to about 10% by weight of an alkyl (58% $C_{14}$, 28% $C_{16}$, 14% $C_{12}$)dimethyl benzyl ammonium halide, 20 to 90% by weight of a lower $C_1$–$C_4$ aliphatic alcohol, 0.1 to 10% by weight of a nonionic surfactant formed by condensing a compound selected from the group consisting of an alkyl phenol, an alkyl amine, an aliphatic alcohol or a fatty acid with ethylene oxide, and a remainder of water.

8. The method of claim 1 wherein the halide is a chloride.

9. The method of claim 1 wherein the lower alcohol is isopropanol.

10. The method of claim 1 wherein the nonionic surfactant is a nonylphenol 9.5 mole ethylene oxide adduct.

* * * * *